US008647884B2

(12) United States Patent
Thomas et al.

(10) Patent No.: US 8,647,884 B2
(45) Date of Patent: Feb. 11, 2014

(54) ORGANIC CHEMICAL SENSOR WITH MICROPOROUS ORGANOSILICATE MATERIAL

(75) Inventors: J. Christopher Thomas, St. Paul, MN (US); Neal A. Rakow, Woodbury, MN (US); John E. Trend, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 105 days.

(21) Appl. No.: 13/141,555

(22) PCT Filed: Dec. 14, 2009

(86) PCT No.: PCT/US2009/067804
§ 371 (c)(1),
(2), (4) Date: Jun. 22, 2011

(87) PCT Pub. No.: WO2010/075014
PCT Pub. Date: Jul. 1, 2010

(65) Prior Publication Data
US 2011/0257038 A1    Oct. 20, 2011

Related U.S. Application Data

(60) Provisional application No. 61/140,180, filed on Dec. 23, 2008.

(51) Int. Cl.
G01N 21/00    (2006.01)
G01N 21/75    (2006.01)
(52) U.S. Cl.
USPC ....................................... 436/164; 422/82.05
(58) Field of Classification Search
USPC ....................................... 436/164; 422/82.05
See application file for complete search history.

(56) References Cited

U.S. PATENT DOCUMENTS

| | | | |
|---|---|---|---|
| 5,143,696 A | 9/1992 | Haas | |
| 5,304,363 A | 4/1994 | Beck | |
| 5,828,542 A | 10/1998 | Riley | |
| 5,857,250 A | 1/1999 | Riley | |
| 5,858,457 A | 1/1999 | Brinker | |
| 5,861,545 A | 1/1999 | Wood | |
| 5,877,895 A | 3/1999 | Shaw | |
| 5,922,299 A | 7/1999 | Bruinsma | |
| 6,180,318 B1 | 1/2001 | Fitzer | |
| 6,248,686 B1 | 6/2001 | Inagaki | |
| 6,270,846 B1 | 8/2001 | Brinker | |
| 6,326,326 B1 | 12/2001 | Feng | |
| 6,329,017 B1 | 12/2001 | Liu | |
| 6,365,266 B1 | 4/2002 | MacDougall | |
| 6,387,453 B1 | 5/2002 | Brinker | |
| 6,396,616 B1 | 5/2002 | Fitzer | |
| 6,566,243 B2 | 5/2003 | Gaynor | |
| 6,592,980 B1 | 7/2003 | MacDougall | |
| 6,630,696 B2 | 10/2003 | Yan | |
| 6,664,071 B1 | 12/2003 | Windhab | |
| 6,696,258 B1 | 2/2004 | Wei | |
| 6,713,643 B2 | 3/2004 | Pinnavaia | |
| 6,818,289 B2 | 11/2004 | MacDougall et al. | |
| 6,882,165 B2 | 4/2005 | Ogura | |
| 6,942,918 B2 | 9/2005 | MacDougall | |
| 7,067,687 B2 | 6/2006 | Pinnavaia | |
| 7,109,130 B2 | 9/2006 | Davis | |
| 7,141,859 B2 | 11/2006 | DeBoer | |
| 7,153,355 B2 | 12/2006 | Sakamoto | |
| 7,307,343 B2 | 12/2007 | Kirner | |
| 7,449,146 B2 * | 11/2008 | Rakow et al. | 422/417 |
| 7,556,774 B2 * | 7/2009 | Rakow et al. | 422/82.05 |
| 2004/0184948 A1 | 9/2004 | Rakow | |
| 2005/0258578 A1 | 11/2005 | Birnbaum | |
| 2005/0282401 A1 | 12/2005 | Davis | |
| 2006/0009575 A1 * | 1/2006 | Nakashima | 524/837 |
| 2006/0032312 A1 | 2/2006 | Auner | |
| 2006/0046079 A1 | 3/2006 | Lee | |
| 2006/0063178 A1 | 3/2006 | Rauh-Adelmann | |
| 2006/0084277 A1 | 4/2006 | Nakashima | |
| 2006/0110940 A1 | 5/2006 | Seon | |
| 2006/0145306 A1 | 7/2006 | Lee | |
| 2006/0159938 A1 | 7/2006 | Lee | |
| 2007/0129613 A1 | 6/2007 | Rochester | |
| 2007/0140907 A1 * | 6/2007 | Rakow et al. | 422/82.08 |
| 2007/0184557 A1 | 8/2007 | Crudden | |
| 2008/0006375 A1 | 1/2008 | Meadows | |
| 2011/0257281 A1 | 10/2011 | Thomas | |

FOREIGN PATENT DOCUMENTS

| | | |
|---|---|---|
| KR | 10-1997-0011025 | 7/1997 |
| KR | 10-0373210 | 2/2003 |
| KR | 10-2003-0086637 | 11/2003 |
| KR | 10-2007-0098414 | 10/2007 |
| WO | WO 94-28372 | 12/1994 |
| WO | WO 2010-075328 | 7/2010 |
| WO | WO 2010-075333 | 7/2010 |

OTHER PUBLICATIONS

Nelson, "Gas Mixtures: Preparation and Control", Lewis Publishers, 1992, Title, Publication and Table of Contents, 6 pgs.
International Search Report for PCT/US2009/069099, mailed Jul. 13, 2010, 3 pages.
International Search Report for PCT/US2009/067804, mailed Aug. 16, 2010, 3 pages.
International Search Report for PCT/US2009/069105, mailed Jul. 26 2010, 3 pages.

* cited by examiner

*Primary Examiner* — Christopher M Babic
*Assistant Examiner* — Valerie Toodle
(74) *Attorney, Agent, or Firm* — Jeffrey M. Olofson

(57) ABSTRACT

Multi-layered optical sensor films are disclosed. The sensor films include a first reflective layer, a detection layer over the reflective layer, and optionally a second reflective layer over the detection layer. The detection layer contains a hydrophobic, amorphous, substantially microporous, analyte-sensitive organosilicate composition. The analyte-sensitive organosilicate composition provides an optical change in the film upon analyte exposure.

29 Claims, 2 Drawing Sheets

ORGANIC CHEMICAL SENSOR WITH MICROPOROUS ORGANOSILICATE MATERIAL

CROSS REFERENCE TO RELATED APPLICATIONS

This application is a national stage filing under 35 U.S.C. 371 of PCT/US2009/067804, filed Dec. 14, 2009, which claims priority to U.S. Provisional Application No. 61/140,180, filed Dec. 23, 2008, the disclosure of which is incorporated by reference in its/their entirety herein.

FIELD OF THE DISCLOSURE

The disclosure relates to sensors and sensing elements, including optical sensors which are suitable for detecting or monitoring organic chemical analytes in an environment. The sensors and sensing elements include microporous organosilicate materials.

BACKGROUND

The development of robust chemical sensors for a range of analytes remains an important endeavor for applications such as environmental monitoring, product quality control, and chemical dosimetry. Among the many methods available for chemical sensing, colorimetric techniques remain advantageous in that the human eye can be used for signal transduction, rather than extensive instrumentation.

Though colorimetric sensors currently exist for a range of analytes, most are based upon employing dyes or colored chemical indicators for detection. Such compounds are typically selective, meaning arrays are necessary to enable detection of various classes of compounds. Moreover, many of these systems have lifetime limitation issues, due to photobleaching or undesirable side reactions. Other optical sensing techniques, such as surface plasmon resonance and spectral interferometry, require substantial signal transduction hardware to provide response, and thus are not useful for simple visual indication.

SUMMARY

The present disclosure provides multi-layered optical sensor films. The sensor films comprise a first reflective layer, and a detection layer over the first reflective layer. In some embodiments, a second reflective layer, over the detection layer may also be present. The detection layer comprises a hydrophobic, amorphous, substantially microporous, analyte-sensitive organosilicate composition. The analyte-sensitive organosilicate composition provides an optical change in the film upon analyte exposure. In some embodiments the first reflective layer is substantially continuous and the second reflective layer is a semi-reflective layer that has an index of refraction different from the index of refraction of the detection layer. At least a portion of the second reflective layer is permeable to an analyte.

In some embodiments, arrays of sensors such as those described above are provided. The sensors may be the same or different, such that they may have different sensitivities to analytes.

In some embodiments, devices are provided. These devices comprise a sensor and a light source. The sensor comprises a first reflective layer, and a detection layer over the first reflective layer. In some embodiments, a second reflective layer over the detection layer may be provided. The detection layer comprises a hydrophobic, amorphous, substantially microporous, analyte-sensitive organosilicate composition. The device may also contain a photo detector.

Also disclosed are methods for detecting analytes. These methods comprise providing a sensor comprising a substantially continuous first reflective layer, and a detection layer over the first reflective layer, the detection layer comprising a substantially microporous, amorphous, hydrophobic, analyte-responsive organosilicate material. In some embodiments, a second reflective layer over the detection layer may be provided, the second reflective layer being a semi-reflective layer having an index of refraction different from the index of refraction of the detection layer, wherein at least a portion of the second reflective layer is permeable to an analyte; providing a light source; contacting the sensor with a medium that may contain an analyte; and monitoring the sensor for a change in optical properties.

DETAILED DESCRIPTION

Figure 1:
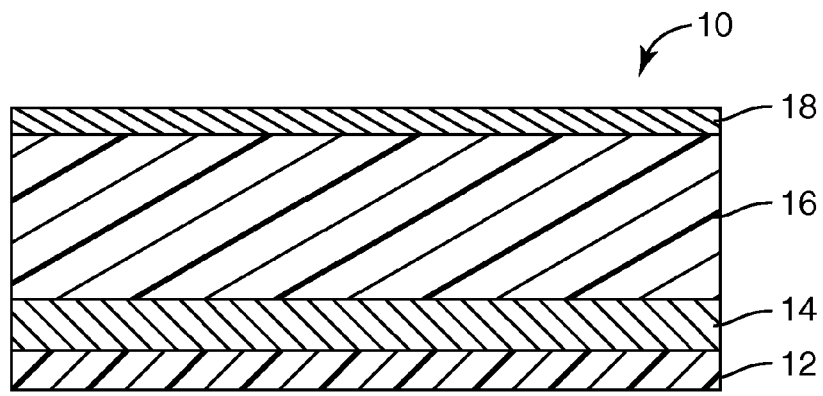
FIG. 1 depicts an exemplary multi-layered film of the present disclosure.

The present disclosure provides multi-layered optical sensor films. The sensor films comprise a first reflective layer, and a detection layer over the first reflective layer. In some embodiments, a second reflective layer over the detection layer may be provided. The detection layer comprises a hydrophobic, amorphous, substantially microporous, analyte-sensitive organosilicate composition. The analyte-sensitive organosilicate composition provides an optical change in the film upon analyte exposure. The multi-layered structure provides a versatile platform for incorporating a variety of chemistries that can detect a range of species. The films can be designed to provide fast, reversible (or, in some cases, permanent) responses.

The multilayer optical sensor films have a number of advantages over conventional optical sensor constructions. For example, in the multi-layer sensor films of this disclosure, the detection layer is hydrophobic and therefore water vapor does not create a substantial change in the optical properties. Also, the films can be readily processed. The reflective layer or layers can be deposited via evaporative or sputter coating, while the detection layer can be deposited via straightforward coating techniques.

As used herein, the term "analyte" means the specific component that is being detected in a chemical or biochemical analysis, typically the analyte is an organic compound or mixture of organic compounds.

As used herein, the term "dimensional change" means a change of distance in a direction normal to the surface of the detection layer surface.

As used herein, the term "porous material" means a material containing a continuous network of pores throughout its volume. Microporous materials are materials that have an average pore diameter of 2 nanometers or less.

As used herein, the term "reflective" means semi-reflective or fully reflective. The term "semi-reflective" means neither fully reflective nor fully transmissive, generally about 30 to about 70% reflective, or about 40 to about 60% reflective.

As used herein, the term "substantially continuous" means a layer of material is non-porous, but may have cracks, grain boundaries, or other structures that create pathways through the layer of material. A "substantially continuous" layer may be non-porous, but permeable to one or more analytes.

As used herein, the term "discontinuous" means a layer of material having at least two separate and distinct islands with empty space therebetween, wherein the at least two separate and distinct islands with empty space therebetween are within a given plane.

As used herein, the term "semicontinuous" means a layer of material that is porous and liquid- or vapor-permeable. A semicontinuous layer may be vapor-permeable but not liquid-permeable.

As used herein, the term "vapor-permeable" when used with respect to a reflective layer one side of which is in fluid communication with a detection layer means that if the other side of the reflective layer is exposed to an air stream containing 1000 ppm styrene monomer vapor flowing at 20 liters/min for 15 minutes, sufficient styrene monomer will pass through the reflective layer so that an optically-responsive change takes place in the detection layer.

As used herein, the term "liquid-permeable" when used with respect to a reflective layer one side of which is in fluid communication with a detection layer means that if the other side of the reflective layer is exposed to a solution containing 10% by volume acetone in water for 10 minutes, sufficient acetone will pass through the reflective layer so that an optically-responsive change takes place in the detection layer.

As used herein, the term "microporous" refers to porous materials that have average pore diameter sizes less than about 2 nanometers.

As used herein, the term "hydrophobic" refers to compositions which do not attract water. The hydrophobic nature of compositions may be measured in a variety of ways, including by the adsorption of water over a given period of time at a given relative humidity. Such a test is defined in greater detail in the Examples section.

As used herein, the term "amorphous" refers to compositions which are substantially non-crystalline. Typically when scanned with a X-ray diffractometer the compositions do not show a discernable X-ray diffraction pattern when scanned from 0.5 to 80 degrees (2θ).

As used herein, the term "organosilicate" refers to compositions that are hybrids containing a covalently linked three dimensional silica network (—Si—O—Si—) with some organo-functional groups R, where R is a hydrocarbon or heteroatom substituted hydrocarbon group linked to the silica network by at least one Si—C bond.

As used herein, the term "hydrocarbon group" refers to a group which contains carbon and hydrogen bonds. A hydrocarbon group may be linear, branched, cyclic, or aromatic. Examples of hydrocarbon groups are alkyl groups and aryl groups.

As used herein, the term "substituted hydrocarbon group" is a hydrocarbon group which contains one or more heteroatoms, such as oxygen, nitrogen, sulfur, phosphorous, boron, a halogen (F, Cl, Br, or I), arsenic, tin or lead. The heteroatoms may be pendant or catenary.

As used herein, the term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, the term "aralkylene" refers to a divalent group of formula —$R^a$—$Ar^a$— where $R^a$ is an alkylene and $Ar^a$ is an arylene (i.e., an alkylene is bonded to an arylene).

As used herein, the term "alkoxy" refers to a group of the formula —OR, where R is an alkyl, aryl, or substituted alkyl group.

As used herein, the term "acetoxy" refers to a group of the formula —OC(O)CH$_3$, where C(O) refers to a carbonyl group C=O.

As used herein, the term "amino" refers to a groups of the formula —NR$_2$, where R is an alkyl, aryl, or substituted alkyl group.

As used herein, the term "pore size" refers to the diameter of a pore and the term "pore volume" refers to the volume of a pore.

As used herein, the term "porogen" refers to a material that facilitates the formation of a porous structure. Solvents typically are not considered to be porogens in this context.

As used herein, the terms "calcine" and "calcination" refers to heating a mixture, such as a sol, to a temperature below the melting point to drive off volatile materials and form an organosilicate network.

As used herein, the term "sol" refers to a precursor mixture containing reactive organosilicate materials in a solvent that forms a continuous organosilicate network upon calcination.

The multi-layered sensor films comprise a first reflective layer, and a detection layer over the first reflective layer. In some embodiments, a second reflective layer over the detection layer is provided. In some embodiments the multi-layer optical sensor films are colorimetric, allowing for detection using visual means without the need for optical equipment. In these embodiments, the sensor films may comprise colored films containing at least one analyte-sensitive organosilicate detection layer between a first reflective layer and an optional second reflective layer, which may both be metal layers. These multi-layered films provide a general means for visual signal transduction. The films function as interference filters, and thus can be highly colored due to reflection of particular wavelengths within the visible range. The coloration of the sensor films is highly dependent upon the thickness of each layer within the stack.

A general depiction of a multi-layered sensor film of the present disclosure is shown in FIG. 1. In general, exemplary multi-layered film sensor 10 comprises (optional) substrate layer 12, first reflective layer 14, detection layer 16, and (optional) second reflective layer 18.

The sensor films can be used for detecting the presence and/or concentration of an analyte or of a mixture of analytes. The analyte may be a gas (e.g., a vapor) or a liquid. The analyte can be a molecule, a macromolecule, a biomolecule, or a biomacromolecule. The analyte may be present in a gaseous medium (such as air) or liquid medium (such as water or other fluids). Typically the analyte is an organic material.

In at least one embodiment, the analyte is detected by a change in optical thickness of the analyte-sensitive organosilicate detection layer upon exposure to the analyte. The analyte passes through an outer or second reflective layer and changes the optical thickness of the detection layer. In one embodiment the analyte is adsorbed into at least a portion of the detection layer. Upon adsorption, color changes (often vivid) can indicate the presence of the analyte.

The change in optical thickness is typically observable in the visible light range and can be detected by the unaided human eye. However, sensors can be designed to show a change in optical thickness when subjected to other light sources such as UV, infrared, or near infrared. Various detection mechanisms can also be used. Examples of suitable detection mechanisms include spectrophotometers, fiber optic spectrophotometers, and photo-detectors, e.g., charge coupled devices (ccd), digital cameras, etc.

In another embodiment, the analyte is detected when its presence causes the delamination of the detection layer from an adjacent layer. Typically, delamination occurs when the analyte wets the interface of the detection layer and an adjacent layer, thereby reducing the interfacial adhesion. When delamination occurs, optical interference is destroyed and the sensor loses perceptible color. This process, which involves changes in the shape of the detection layer that reduce the interfacial area with adjacent layers, causes defects within the material which permanently change the optical properties of the sensor film.

The multi-layer optical sensor may comprise a substrate. The substrate is optional, but when present it may comprise any suitable material capable of providing support for the multi-layer optical sensor. It may be flexible or non-flexible. The substrate material can be tailored to the application. Often it is suitable to use in a vacuum deposition process.

The first reflective layer may comprise any material that can form a fully reflective or semi-reflective layer. Typically, the material has a thickness of about 5 nanometers to about 1 micrometer. In some embodiments the thickness is about 20 to about 200 nm. Thinner layers can typically be used to make the first reflective layer semi-reflective. Although the first reflective layer is typically made to be more reflective than the second reflective layer, sometimes it is desirable to have the reflectivity of the first reflective layer and second reflective layer be the same so a response to the presence of an analyte can be seen from either side of the sensor film.

Suitable materials for the first reflective layer include metals or semi-metals such as aluminum, chromium, gold, nickel, silicon, silver, titanium, palladium, and platinum. Other suitable materials that may be included in the first reflective layer include metal oxides such as chromium oxide and titanium oxide.

In some exemplary embodiments, the first reflective layer is at least about 90% reflective (i.e., at least about 10% transmissive), and in some embodiments, about 99% reflective (i.e., about 1% transmissive). In other exemplary embodiments, the first reflective layer is a semi-reflective layer, wherein the first reflective layer is at least about 20% reflective, such as about 20 to about 90% reflective, or about 30 to about 70% reflective.

In some embodiments, the first reflective layer also acts as the substrate, providing support for the sensor. The first reflective layer may be a substantially continuous layer or a discontinuous layer. Further, the first reflective layer may comprise one or more reflective layers. Generally, the first reflective layer comprises a single reflective layer.

The detection layer comprises a hydrophobic, amorphous, substantially microporous, analyte-sensitive organosilicate composition. In most embodiments, the detection layer changes optical thickness upon exposure to an analyte. The change in optical thickness can be caused by a dimensional change such as a change in physical thickness of the layer due to swelling or shrinkage or a change in refractive index of the detection layer due to the presence or chemical reaction of the analyte. The detection layer may change from one color to another, from a color to no color, or from no color to a color.

Organosilicate compositions are hybrid compositions that contain a silica framework as well as organo-functional groups. The organosilicate compositions comprise $RSiO_3$ units linked through bridging Si—O—Si linkages, where R may be a hydrocarbon group or substituted hydrocarbon group. The R group is bonded to the silica matrix by a covalent Si—C bond.

The organosilicate compositions of this disclosure may be described as having a relatively high organic content. The relatively high organic content of the organosilicate compositions is a desirable feature because, as is discussed below, it affects the hydrophobicity of the organosilicate compositions. The relatively high organic content may be achieved in a number of ways. For example, there may be many $RSiO_3$ units present with R being relatively small hydrocarbon groups such as methyl, ethyl, propyl, etc. to give a high organic content or there may be fewer $RSiO_3$ units with R being relatively large hydrocarbon groups such as aryl.

A wide variety of organo-functional groups (R groups in the $RSiO_3$ units) are suitable for use in the organosilicate compositions. The organo-functional groups may be simple alkyl or alkylene groups such as methyl, ethyl, propyl, methylene, ethylene, propylene, and the like or more complex alkyl groups such as. The organo-functional groups may also be aromatic groups such as aryl, substituted aryl or the like. In some embodiments, the R group may be alkylene or arylene group that links two $SiO_3$ units (e.g. —$O_3$Si—R—$SiO_3$—). Examples of suitable aryl and arylene groups include, for example, phenyl, tolyl, naphthyl, phenylene, tolylene, bisphenylene, and the like.

In some embodiments, the organosilicate compositions may contain at least some aromatic content (i.e. aryl and/or arylene groups). Arylene groups, where the arylene group is linked to 2 silicon atoms, are particularly suitable because it is believed that the rigid aromatic rings help to provide the desirable pore structure. Among the particularly suitable aryl and arylene groups are phenyl, naphthyl, and bisphenylene.

The organo-functional nature of the organosilicates tend to render the compositions hydrophobic, since organic groups are naturally oleophilic (literally "oil loving") and are more compatible with other organo-functional species than with water. The hydrophobic nature of the compositions makes these materials less likely to adsorb moisture from the atmosphere. The adsorption of moisture from the atmosphere is undesirable, especially in instances where these materials are utilized in sensor applications where sensing of organic molecules is desired. If the pores were to substantially adsorb moisture from the environment, the ability of the pores to adsorb organic analytes of interest would be diminished. However, since the compositions are hydrophobic, this renders them relatively unaffected by moisture from the environment.

Hydrophobicity can be measured in a variety of ways. One technique that is particularly useful is to expose the hydrophobic, amorphous, substantially microporous, organosilicate compositions to an environment with a given relative humidity, such as 50% relative humidity at room temperature, for a sufficient period of time such that the adsorbed water and water in the atmosphere are at equilibrium. This equilibrium state can be determined by plotting a graph of time versus adsorption and observing where the profile curve plateaus. Typically the film adsorbs water into less than 75% of the available pore volume at relative humidity of 50% at equilibrium. In some embodiments, the film adsorbs water into less than 65% or even less than 50% of the available pore volume at a relative humidity of 50% at equilibrium. In some embodiments the film adsorbs water into less than 30% of the available pore volume at a relative humidity of 50% at equilibrium.

The organosilicate compositions are amorphous or substantially amorphous, meaning that they are free or essentially free of crystallinity. While not wishing to be bound by theory, it is believed that amorphous organosilicates contain more diverse porous structures making them suitable for a wide range of analytes in, for example, sensing applications.

The amorphous nature of the organosilicate compositions can be determined, for example, through the use of an X-ray diffractometer. Typically, when scanned with a X-ray diffractometer, the compositions do not show a discernable X-ray diffraction pattern when scanned from 0.5 to 80 degrees (2θ). By no discernable X-ray diffraction pattern it is meant that X-ray diffraction data are essentially featureless, indicating no evidence for the presence of structural order.

The organosilicate compositions are substantially microporous. Porous materials have been classified in many different ways. The IUPAC definitions for porous materials define porous materials with an average pore diameter of less than 2 nanometers as microporous, porous materials with an average pore diameter of from 2-50 nanometers as mesoporous, and porous materials with an average pore diameter of greater than 50 nanometers as macroporous. In the organosilicate compositions of this disclosure, at least 50% of the total pore volume comprises pores with a diameter of 2.0 nanometers or less. In some embodiments at least 50% of the total pore volume comprises pores with a diameter of 0.6-1.3 nanometers.

In some embodiments, the detection layers of this disclosure can be described as organosilicate films, these organosilicate films are prepared from precursor mixtures which typically do not contain porogens. In this context porogens refer to chemical compounds added to the precursor mixture to aid in the formation of the porous structure. Solvents and other components added to the reaction mixture for a different purpose are not considered to be porogens. In other embodiments optional porogen may be added if desired.

Typically a precursor mixture is prepared, coated on a substrate and heated to dry and/or calcine the precursor mixture to form a hydrophobic, amorphous, substantially microporous, organosilicate film.

The precursor mixture may contain a variety of different materials. Among the suitable materials are solvents, at least two hydrolysable silanes, optional porogen, and acids. In some embodiments the precursor mixture may contain optional polymeric species which may be porous or non-porous as long as the polymeric species do not interfere with the formation of the microporous organosilicate network. Examples of such polymeric species include, for example, polyfurfuryl alcohols, polysaccharides, polyethers, polyolefins, polystyrenes and the like.

Typically the precursor mixture contains at least one solvent. The solvent or solvents function to solubilize and dilute the reactants and as a reaction medium for the hydrolysis and condensation reactions that occur in the precursor mixture. The solvent should be able to at least partially solubilize the reactants. Typically the solvent is at least partially miscible with water, since often aqueous reagents such as aqueous acids are used. Suitable solvents include, for example: alcohols such as methanol, ethanol, isopropanol, tert-butanol; ketones such as acetone and methyl ethyl ketone; ethers such as tetrahydrofuran; esters such as ethyl acetate; amides such as dimethylformamide; or mixtures thereof.

The precursor mixture contains at least one hydrolysable silane. Hydrolysable silanes are compounds of the general formula $R_n$—$\{Si(Z)_{4-n}\}_x$ where R is an x-valent hydrocarbon or substituted hydrocarbon group, x is an integer of 1 or greater, Z is a hydrolysable group, and n is an integer of 1, 2 or 3. Suitable hydrolysable groups include alkoxy, halo, acetoxy, and amino groups. In some embodiments x is 1, n is 1, the R group is a hydrocarbon group such as an alkyl or aryl group, and Z is an alkoxy. In other embodiments, x is 2, n is 1, R is an alkylene, arylene, aralkalene group, and Z is an alkoxy.

In some embodiments, the precursor mixture contains at least two hydrolysable silanes. In some embodiments, the precursor mixture contains a hydrolysable silane of the general structure $R^1$—$Si(OR^2)_3$ as well as a hydrolysable silane of the general structure $(R^3O)_3Si$—$R^5$—$Si(OR^4)_3$ where $R^1$, $R^2$, $R^3$, and $R^4$, are alkyl or aryl groups, and $R^5$ is an alkylene, arylene or aralkylene group. Examples of suitable hydrolysable silanes include, for example methyl trimethoxy silane, ethyl trimethoxy silane, phenyl trimethoxy silane, 4,4'-bis(triethoxysilyl)-1,1'-biphenyl, and the like. In some embodiments the precursor mixture contains phenyl trimethoxy silane and 4,4'-bis(triethoxysilyl)-1,1'-biphenyl.

The amount of hydrolysable silanes present in the precursor mixture will vary depending upon the nature of the hydrolysable silane or silanes and the desired properties of the formed organosilicate composition. Typically, hydrolysable silanes are present in the range of about 5-25 weight % based upon the total weight of the precursor mixture.

The precursor mixture contains an acid to facilitate the hydrolysis and condensation reactions of the hydrolysable silanes. Any suitable acid can be used as long as it is compatible with the precursor mixture and aids in the hydrolysis reaction. Examples of suitable acids include, for example, organic acids, phosphonium acids, ammonium acids and mineral acids. Organic acids include, for example, carboxylic acids such as acetic acid, sulfonic acids such as alkyl sulfonic acids, phosphonic acids such as alkyl phosphonic acids of the general formula $RP(O)(OH)_2$ where R is an alkyl group, and phosphinic acids such as alkyl phosphinic acids of the general formula $R_2P(O)(OH)$ where each R independently is an alkyl group. Phosphonium acids include compounds of the type $R_3PH^+$ where each R independently is a hydrogen or an alkyl or an aryl group.

Ammonium acids include compounds of the type $R_3NH^+$ where each R independently is a hydrogen or an alkyl or an aryl group. Mineral acids are inorganic acids that include, for example, hydrochloric acid, nitric acid, sulfuric acid, boric acid, phosphoric acid, hydrofluoric acid and the like. Typically mineral acids are used in their aqueous form, that is to say, the acid is dissolved in water. Generally, due to their availability and ease of use, aqueous mineral acids are used. In some embodiments the acid is aqueous hydrochloric acid.

The precursor mixture may optionally contain at least one porogen. Porogens are materials that facilitate the formation of a porous structure. The porogen does not become covalently attached to the organosilicate composition and typically is removed from the organosilicate composition mixture during or after calcination. Generally the porogen does not contain any functional groups that react with the reactive species in the precursor mixture.

Examples of suitable porogens include polyether surfactants, alkyl ammonium salts, hydrocarbons such as 1,3,5-trimethyl benzene and the like. In some embodiments the porogen is an ammonium salt such as, for example, an alkyl ammonium salt with a halide counterion. Examples of such salts include tetramethylammonium chloride, tetraethylammonium chloride, tetrapropylammonium chloride, tetra-n-butylammonium chloride, octyltrimethylammonium bromide, decyltrimethylammonium bromide, cetyltrimethylammonium bromide, and the like. One particularly suitable porogen is octyltrimethylammonium bromide. Typically the porogen is present in the precursor mixture in amounts ranging from 1-25 weight %.

Other optional additives can be added to the precursor mixture as long as they do not interfere with the formation of the microporous structure. In particular, especially if an aqueous acid is not used, water may be added to the precursor mixture.

The precursor mixture can be deposited on a substrate to form a layer. The substrate may form a portion of the sensor element or it may be a temporary substrate such that the precursor forms a preformed film of analyte-sensitive organosilicate material. The precursor may be deposited on a substrate using a variety of coating techniques such as, for example spin coating, dip coating, roll coating, spray coating and printing techniques including, for example, inkjet printing and screen printing. Spin coating is particularly useful.

The substrate may be any suitable substrate upon which it is desirable to prepare an organosilicate layer and which can withstand the calcination step to form the organosilicate layer. Examples of substrates include, for example, metal and metal oxide plates and foils, glass plates, ceramic plates and articles, silicon wafers, polymers capable of withstanding the calcination step such as polyimides and silicones, and the like. In some embodiments, the substrate is the first reflective layer of the sensor.

Once the precursor mixture is coated on a substrate it is typically subjected to a heat treatment to dry and calcine the mixture. The heating step may be to a relatively low temperature such as for example 30-100° C. Generally the heating step involves higher temperatures. Typically the coated precursor mixture is heated to a temperature in the range of about 200° C. to about 500° C. In some embodiments the heating step is to about 450° C.

Following the heat treatment additional optional processing steps may be carried out. For example, it may be desirable to treat the organosilicate film with a treating agent. The treating agent can further modify the organosilicated film to make it, for example, more hydrophobic. An example of a suitable treating agent is an organosilane treating agent such as a alkyl disilazane such as hexamethyl disilazane. Such a treatment can be carried out by exposing the layer to vapors of hexamethyl disilazane.

The detection layer can have any desired overall thickness. Desirably, the detection layer has an overall thickness of more than about 50 nm, such as in the range of about 100 to about 1000 nm. In one embodiment, the detection layer has a layer thickness that is substantially the same throughout the detection layer. See, for example, detection layer 16 of FIG. 1. In other embodiments, the detection layer has a layer thickness that varies from a first location within the detection layer to one or more other locations within the detection layer. Additionally, the detection layer may be discontinuous or patterned. The second reflective layer applied over the detection layer may be applied so as to conform to the thickness variations and/or pattern in the detection layer.

The optional second reflective layer may comprise any material that can form a permeable, reflective or semi-reflective layer and has a different index of refraction than the detection layer. In most embodiments, it is preferable that the material is semi-reflective at a thickness of about 5 nm because at this thickness most analytes will be able to permeate through this layer to the detection layer. Desired thicknesses will depend on the material used to form the layer, the analyte to be detected, and the medium that will carry the analyte.

Suitable materials include metals and semi-metals such as aluminum, chromium, gold, nickel, silicon, silver, titanium, palladium, and platinum. Other suitable materials that may be included in the second reflective layer include oxides such as aluminum oxide, titanium oxide, and chromium oxide.

Like the first reflective layer, the second reflective layer may be a substantially continuous layer or a discontinuous layer. Further, like the first reflective layer, the second reflective layer may comprise one or more reflective or semi-reflective layers. Generally, the second reflective layer comprises a single semi-reflective layer, which is either substantially continuous or discontinuous.

In one exemplary embodiment, the second reflective layer is a substantially continuous layer. In this embodiment, the construction and composition of the second reflective layer may be substantially consistent across an upper surface of and throughout the second reflective layer. Alternatively, the construction and/or composition of the second reflective layer may vary across an upper surface of and throughout the second reflective layer. For example, the second reflective layer may have a differential permeability such that the second reflective layer has higher analyte permeability for a given analyte at a first location on an upper surface of the second reflective layer and lower analyte permeability for the same analyte at a second location on the upper surface. The first and second locations on the upper surface of the second reflective layer may be randomly positioned relative to one another, or may form a pattern on the upper surface.

The substantially continuous second reflective layer may also have a pattern therein wherein first regions of the second reflective layer have a greater light reflectance than second regions of the second reflective layer. The first and second regions on the second reflective layer may form a pattern on the upper surface of and within the second reflective layer. A patterned second reflective layer may comprise a pattern so as to create colored images, words, or messages upon exposure of the underlying detection layer to an analyte. The second reflective layer can provide easily identifiable warnings for a user upon exposure to an analyte.

Any number of methods may be used to alter the permeability of the second reflective layer and/or create a pattern on and within the second reflective layer. Suitable methods include, but are not limited to, spatially controlling the deposition conditions of the second reflective layer to vary the thickness or density of the second reflective layer. For example, a mask can be placed between the deposition source and the substrate such that the thickness of deposited second reflective layer varies from a first location to a second location on an upper surface. The differential permeability and/or creation of a pattern on and within the second reflective layer can also be produced by post-treatment of the second reflective layer with localized energy inputs such as laser treatment to change the microstructure of the second reflective layer.

Any of the above-mentioned methods may be used to create one or more patterns on the second reflective layer. The choice of a given pattern or patterns may depend on a number of factors including, but not limited to, the analyte or analytes of interest, the semi-reflective material or materials used, the message, if any, displayed to a user, or a combination thereof.

Exemplary multi-layered films having a substantially continuous second reflective layer are shown in FIG. 1. In one exemplary multi-layered film sensor, the multi-layered film sensor comprises a substantially continuous second reflective layer over a detection layer, wherein the detection layer has an increased surface area for potentially enhanced detection of an analyte due the presence of one or more wells within the detection layer. Desirably, the substantially continuous second reflective layer positioned over the detection layer containing wells is a single layer of semi-reflective material.

In a further exemplary embodiment, the second reflective layer is a discontinuous layer. In this embodiment, the composition of the second reflective layer may be substantially consistent across the second reflective layer; however, areas separate the second reflective layer into two or more discontinuous regions. The discontinuous second reflective layer may comprise any pattern of semi-reflective islands within a "sea" of exposed areas (i.e., the detection layer is exposed). The size and density of semi-reflective islands on the detection layer may vary as desired, and may be uniformly dispersed or non-uniformly dispersed over an upper surface of the detection layer. Typically, the semi-reflective islands are uniformly dispersed over an upper surface of the detection layer and have at least one dimension (i.e., length, width, or diameter) of at least about 1.0 micrometer, desirably, from about 10.0 to about 100 micrometers; however, any semi-reflective island size, shape, and density may be used. Further, the exposed areas typically have at least one dimension (i.e., length, width, or diameter) ranging from about 1.0 to about 100 micrometers; however, the exposed areas may have any dimensions.

One suitable method for providing a discontinuous second reflective layer over a detection layer comprises a laser ablation method. Portions of the second reflective layer may be removed by exposing the portions to a laser as described in U.S. Pat. Nos. 6,180,318 and 6,396,616. Another exemplary method that could be used to produce a discontinuous second reflective layer is a photo-imaging method.

In one embodiment, the discontinuous second reflective layer comprises a number of semi-reflective islands uniformly dispersed over an upper surface of the detection layer, wherein each semi-reflective island has an upper surface area in the shape of a square or circle having a length, width, or diameter of at least about 1.0 micrometer, more desirably, from about 10.0 to about 100 micrometers. It should be understood that each semi-reflective island may have an upper surface area in a variety of shapes including, but not limited to, triangular, rectangular, star-shaped, diamond-shaped, etc., and one or more dimensions of at least about 1.0 micrometer, more desirably, from about 10.0 to about 100 micrometers. Further, it should be understood that each semi-reflective island may be either permeable or impermeable to one or more analytes. When the semi-reflective islands are permeable to one or more analytes, the sensor allows one or more analytes to contact the detection layer directly through exposed areas, as well as indirectly through the semi-reflective islands.

A laser ablation method (such as described in U.S. Pat. Nos. 6,180,318 and 6,396,616), a chemical etching method, or another method could be used to remove portions of the second reflective layer, as well as portions of the detection layer to form wells that extend from an upper surface of the second reflective layer into the detection layer, and possibly to an upper surface of the first reflective layer (or an upper surface of the optional substrate). In this embodiment, the resulting structure comprises an array of multi-layered film islands (e.g., square islands having 100 micrometer sides within a grid of exposed areas having a width of about 10 micrometers) having the same detection layer composition and second reflective layer composition. The second reflective layer each island can be either permeable or impermeable to one or more analytes. When the semi-reflective islands are permeable to one or more analytes, the multilayer structures enable penetration of an analyte into the detection layer from the sides of the detection layer, as well as from the top of the detection layer. The size, shape and density of multi-layered film islands within the resulting structure may vary similarly to the semi-reflective islands described above. Typically, each multi-layered film island has one or more dimensions of at least about 1 micrometer such as about 10.0 to about 100 micrometers.

In addition to the above-described methods, multi-layered film islands may also be formed by depositing islands of detection layer material onto a first reflective layer and then depositing a second reflective layer on top of each detection layer island. Various printing techniques including, but not limited to, ink-jet printing and contact printing, may be used to deposit the detection layer in island or patterned form onto the first reflective layer.

The semicontinuous first or second reflective layer may comprise metallic nanoparticles. The nanoparticle metallic layer or layers may be a reflective or semi-reflective layers. For example, a second reflective layer may be formed by applying a dilute coating solution or suspension of metal nanoparticles to the detection layer and allowing the solution or suspension to dry to form a semicontinuous liquid- or vapor-permeable light-reflective layer. The dilution level may, for example, be such as to provide a coating solution or suspension that will provide a suitably liquid- or vapor-permeable metal nanoparticle layer, for example solids levels less than 40 wt. %, less than 30 wt. %, less than 20 wt. %, less than 10 wt. %, less than 5% or less than 4%. By diluting an as-received commercial metal nanoparticle product with additional solvent and applying and drying the dilute solution or suspension, an appreciably thin, liquid- or vapor-permeable layer can be obtained. A variety of coating techniques can be employed to apply the metal nanoparticle solution or suspension, including swabbing, dip coating, roll coating, spin-coating, spray coating, die coating, ink jet coating, screen printing (e.g., rotary screen printing), gravure printing, flexographic printing and other techniques that will be familiar to persons having ordinary skill in the art. Spin-coating may provide a thinner, more permeable coating than is obtained using other methods. Accordingly, some silver nanoparticle suspensions available at low solids levels (such as 5 wt. % SVW001 silver from Nippon Paint or 10 wt. % SILVERJET DGP-40LT-25C from Advanced Nano Products) might be usable in the as-received form without further dilution if spin-coated at an appropriately high speed and temperature onto a suitable substrate. The metal nanoparticle layer may be sintered after it has been applied (e.g., by heating at about 125 to about 250° C. for about 10 minutes to about 1 hour) so long as the sintering does not cause a loss of adequate permeability. It will be understood that the resulting reflective layer may no longer contain readily-identifiable nanoparticles, but that it may be referred to as a nanoparticle reflective layer to identify the manner in which it has been made.

The sensor film may comprise additional layers between any of the previously described layers, as long as the additional layer (or layers) does not interfere with the optics of the sensor film. Additional layers could include tie layers, structural layers, etc.

The sensor film may also include additional layers above the second reflective layer. Suitable additional layers that may at least partially cover the second reflective layer include, but are not limited to, a transparent layer or laminate, and a masking layer to temporarily or permanently shield a portion of the second reflective layer from exposure to one or more analytes. The additional layers may be applied directly onto the second reflective layer or may be temporarily or permanently bonded to the second reflective layer via a tie layer or other adhesive layer. If necessary, an outer surface of the second reflective layer may be treated (e.g., chemically etched or primed, electrical discharge treatment, etc.) to enhance the bond to additional layers.

In one exemplary embodiment, a masking layer is provided over the second reflective layer in the form of a pattern. In this embodiment, upon exposure to an analyte, the sensor displays a signal in the form of a pattern (i.e., a reverse pattern of the masking layer on the second reflective layer). The signal pattern may have any desired configuration including, but not limited to, shapes, letters, words, a specific message to the user, safety instructions to the user, a company logo, etc.

The multi-layered films of the present disclosure may be used alone or may be part of a device for detecting the presence and/or concentration of one or more analytes. In one embodiment, the multi-layered film sensor is at least partially enclosed by a housing. The housing desirably comprises at least one opening positioned above the second reflective layer so that the second reflective layer is viewable through the at least one opening. In some embodiments, the housing comprises at least one opening, wherein the at least one opening provides a restricted view of an upper surface of the second reflective layer so as to minimize any potential change in the viewable color of the sensor (and confusion of the user as to the sensor reading) due to the angle of view. Typically, the restricted view allows a view of the upper surface of the second reflective layer within an angle of ±30°, more desirably, ±15° from a normal view (i.e., a view from a position perpendicular to the outer surface of the second reflective layer).

The housing (or the optional substrate described above) may also be used to constrain the multi-layered film sensor of the present disclosure so that the film is in an arched or cylindrical shape. Such a configuration allows a user to view the sensor from a larger range of viewing angles with minimal shift in color.

As discussed above, the multi-layered film sensors of the present disclosure may possess a substantially continuous second reflective layer or a discontinuous second reflective layer. In one exemplary embodiment, the sensor comprises a substantially continuous first reflective layer; a detection layer over the first reflective layer, wherein the detection layer comprises a substantially microporous, amorphous, hydrophobic, analyte-responsive organosilicate material; and a substantially continuous second reflective layer over the detection layer, wherein the second reflective layer has an index of refraction different from the index of refraction of the detection layer and is permeable to a given analyte. Desirably, the substantially continuous first reflective layer, the substantially continuous second reflective layer, or both, comprise a single layer of reflective or semi-reflective material to minimize the thickness of either or both layers so that one or more analytes can permeate either or both layers.

In a further exemplary embodiment, the sensor comprises a first reflective layer; a detection layer over the first reflective layer; and a discontinuous second reflective layer over the detection layer, wherein the second reflective layer has an index of refraction different from the index of refraction of the detection layer. In this exemplary embodiment, the sensor desirably possesses at least one of the following features:

(a) the discontinuous second reflective layer comprises a single layer of semi-reflective islands;

(b) the discontinuous second reflective layer comprises a single layer of semi-reflective islands having at least one dimension greater than 10 micrometers, and exposed areas between the semi-reflective islands, wherein the exposed areas have a width of at least 1.0 micrometer;

(c) the detection layer contains wells extending a depth into the detection layer.

The multi-layered films of the present disclosure can be created via methods such as the process described, e.g., in U.S. Pat. No. 5,877,895. The detection layers may also be made by spin-coating, solution coating, extrusion coating, or other suitable techniques known in the art. The first reflective layer and second reflective layer may be made by standard vapor coating techniques such as evaporation, sputtering, chemical vapor deposition (CVD), plasma deposition, or flame deposition. Another method for making the first reflective layer and second reflective layer is plating out of solution.

The film sensors may be used in a system comprising the sensor, a light source, and, optionally, a means of monitoring the sensor for a change of color. The light source can be a natural or artificial light source. The monitoring can be done in a variety of ways. It could be done visually, with a photodetector, or by other suitable means.

The analyte may be present in a vapor or liquid medium. For example, an analyte may be present in the atmosphere or in a liquid solvent. In either case, in many embodiments, at least a portion of the analyte permeates through the second reflective layer of the film sensor to interact with the detection layer.

Two or more film sensors may be used together to form an array. The array may be in any suitable configuration. For example, an array may comprise two or more sensors side by side, or sensors may be attached to, or constructed on, opposite sides of a substrate. The sensors within a given array may be of the same type or may be different. Arrays of multi-layered film sensors would be useful for identification of analytes, based upon their unique response signatures from the array in aggregate, as opposed to only detecting the presence of a chemical agent.

Arrays of multi-layered film sensors may have different detection layer pore size distributions, or different detection layer thicknesses within a given stack, or a combination thereof, so as to detect the presence and/or concentration of one or more analytes in a given sample medium.

In some embodiments, the array comprises two or more sensors, wherein each sensor in the array (a) shares a common first reflective layer and (b) comprises a multi-layered film island comprising a stack of layers including a detection layer with a substantially microporous, amorphous, hydrophobic, analyte-responsive organosilicate material, and a second reflective layer with a semi-reflective layer composition. Generally, the detection layer composition is similar for each sensor in the array and the semi-reflective composition is similar for each sensor in the array.

The film sensors of the present disclosure have many useful applications. They can be used, e.g., to detect a wide range of organic vapors. The sensors may be used to detect the presence and/or concentration of a given analyte within a solution or gas. Sensor arrays may be used to detect the presence and/or concentration of one or more analytes within a solution or gas. In one possible application, the multi-layered film sensors provide an overall color pattern to a user based on the interaction of a liquid or gas medium with the array, rather than on the interaction of a liquid or gas medium with a single sensor element.

Prior to use, the multi-layered film sensors are substantially free of an analyte to be detected. The "unexposed" multi-layered film sensor prior to use typically either displays a first color, or is colorless when viewed through the second reflective layer. Upon exposure to one or more analytes to be detected, the "unexposed" multi-layered film sensor converts to an analyte-containing sensor. The analyte-containing sensor either displays a second color that is different from the first color, undergoes a color change from a first color to a colorless condition, undergoes a color change from a colorless condition to a color-containing condition, or undergoes some other detectable optical change such as a change in the wavelength of a spectral maximum or minimum when monitored by optical spectroscopy.

Any of the above-described sensors and arrays of sensors may be used to detect one or more analytes in a given medium. In one exemplary method of detecting of analyte, the method detects the presence or absence of an analyte, wherein the method comprises providing a sensor (or array of sensors), providing a light source, contacting the sensor (or array of sensors) with a medium that may contain an analyte, and monitoring the sensor (or array of sensors) for a change in optical properties. As discussed above, the medium may be a liquid or a gas. Further, the one or more analytes may permeate through the second reflective layer, the first reflective layer, or both layers.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| OTAB | octyltrimethylammonium bromide |
| BTSBP | 4,4'-bis(triethoxysilyl)-1,1'-biphenyl |
| PTMS | phenyl(trimethoxy)silane |
| HMDS | hexamethyldisilazane |
| Silicon Wafers | P<100>, 0-100 Ω · cm 500 ± 20 μm thickness silicon wafers, commercially available from University Wafers, cut into 25 × 25 mm² sections and cleaned with acetone prior to use. |

Test Methods

Determination of Pore Sizes

Determination of pore size was done using nitrogen adsorption measurements. Material to be tested was coated on a 100 mm diameter Silicon Wafer. The wafer was coated repeatedly using the spin-coating method and subsequently calcined as described in the Example. The film was recovered and used for nitrogen adsorption measurements. Total pore volume was measured by nitrogen adsorption using a gas adsorption analyzer available under the trade designation "QUANTACHROME AUTOSORB IC" (Quantachrome Instruments, Boynton Beach, Fla.) operated according to the manufacturer's directions using a 74 point micro pore analysis.

Hydrophobicity Determination

Coated sensor pieces were placed into a controlled humidity test system and were monitored by optical spectroscopy. An Ocean Optics fiber optic probe, LS-1 light source and USB-2000 spectrophotometer were used for monitoring the sensor. Air streams were generated at controlled percentages of relative humidity by flowing the air through a thermostatted container of water. The sensors were exposed to the humid air at a flow rate of 2.5 Liters/minute, and the reflected optical spectrum between 400 nm and 800 nm was observed. Subsequently, the change in the wavelength of the spectral maximum (or minimum) was plotted as a function of the concentration of the vapor. A larger wavelength shift correlates to a larger amount of water vapor adsorption into the porous material.

The amount of water filling the pores at 50% relative humidity was determined using the following procedure. The amount of water present in the pores at 50% relative humidity at equilibrium was compared to the amount of water present when the pores are empty of water and when the pores are essentially filled with water. To make these comparisons the assumptions were made that the pores are essentially empty under relatively low relative humidity (approximately 5% relative humidity) and the pores are essentially full at equilibrium under an 85% relative humidity environment. The difference in optical peak positions were measured under 5%, 50% and 85% relative humidity. The difference in the peak positions between samples at 5% and 50% relative humidity is reported as $\Delta_{50}\%$, the difference in peak shift between samples at 5% and 85% relative humidity is reported as $\Delta_{85}\%$. The ratio of these 2 values, $\Delta_{50}\%/\Delta_{85}\%$, gives a value that is indicative of the amount of water present in the pores at 50% relative humidity. Multiplying this ratio by 100% gives a percentage of pores filled with water at 50% relative humidity at equilibrium.

Vapor Exposure Method

Coated sensor pieces were placed into a controlled vapor delivery system and were monitored by optical spectroscopy. An Ocean Optics fiber optic probe, LS-1 light source and USB-2000 spectrophotometer were used for monitoring the sensor. The reflected optical spectrum between 400 nm and 800 nm was observed. A controlled concentration of vapor in air was introduced to the coated section at a flow rate of approximately 2.5 Liters/minute, and the spectral response was monitored. Subsequently, the change in the wavelength of the spectral maximum (or minimum) was plotted as a function of the concentration of the vapor. A larger wavelength shift correlates to a larger amount of vapor adsorption into the porous material.

Organic Vapor Sensing

To demonstrate the use of these materials for organic vapor sensing applications, the materials were exposed to different concentrations and monitored by the Vapor Exposure Method above.

X-Ray Scattering

Samples were tested for X-ray scattering to determine the amorphous nature of the sample. Reflection geometry data were collected in the form of a survey scan by use of a Philips vertical diffractometer, copper $K_\alpha$ radiation, and proportional detector registry of the scattered radiation. The diffractometer was fitted with variable incident beam slits, fixed diffracted beam slits, and graphite diffracted beam monochromator. The survey scan was conducted from 5 to 80 degrees ($2\theta$) using a 0.04 degree step size and 4 second dwell time. X-ray generator settings of 45 kV and 35 mA were employed. Additional reflection geometry low angle data were collected by use of a Huber 4-circle diffractometer, copper $K_\alpha$ radiation, and scintillation detector registry of the scattered radiation. The incident beam was collimated to a 700 µm pinhole and nickel filtered. Scan was conducted from 0.5 to 15 degrees ($2\theta$) using a 0.01 degree step interval and 60 second dwell time. X-ray generator settings of 40 kV and 20 mA were employed.

Synthesis Examples

Preparation of Reagent Solutions

A series of reagent solutions were prepared that were used to prepare the precursor mixtures in the examples below.

Solution 1

In a polyethylene bottle was combined OTAB (0.126 gram), ethanol (2.102 grams), BTSBP (0.492 gram), and 0.1 Molar HCl (aq) (0.201 gram).

Solution 2

In a polyethylene bottle was combined OTAB (0.127 gram), ethanol (2.129 grams), BTSBP (0.445 gram), PTMS (0.052 gram), and 0.1 Molar HCl (aq) (0.199 gram).

Solution 3

In a polyethylene bottle was combined OTAB (0.124 gram), ethanol (2.106 grams), BTSBP (0.392 gram), PTMS (0.102 gram), and 0.1 M HCl (aq) (0.205 gram).

Solution 4

In a polyethylene bottle was combined OTAB (0.126 gram), ethanol (2.112 grams), BTSBP (0.352 gram), PTMS (0.154 gram), and 0.1 M HCl (aq) (0.203 gram).

Solution 5

In a polyethylene bottle was combined OTAB (0.127 gram), ethanol (2.095 grams), BTSBP (0.300 gram), PTMS (0.201 gram), and 0.1 M HCl (aq) (0.201 gram).

Examples 1-5

Figure 2:
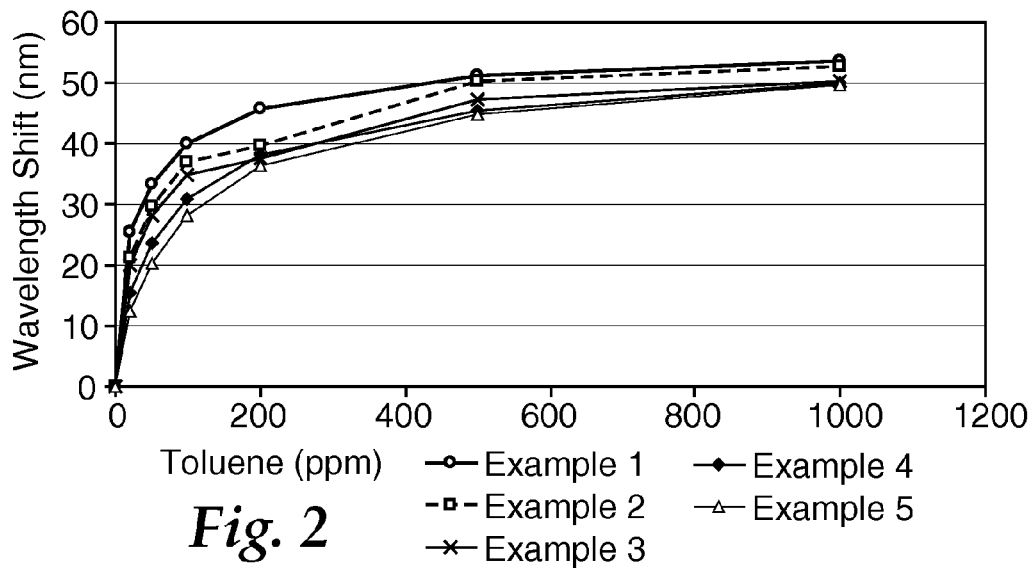
FIG. 2 is a plot of the measured wavelength shift of an exemplary sensing element at various exposure levels of the organic analyte toluene.

For Examples 1-5, the solutions shown in Table 1 were used. The solutions were spin coated onto Silicon Wafers using a Headway Research EC101 DT-R790 spin-coater with a 2 centimeter diameter chuck. Each Silicon Wafer section was flooded with several drops of solution prior to spinning The spin-coating was performed at 1000 rpm for 60 seconds. Coated sections were calcined in air in a box furnace at a rate of 1° C./min to a temperature of 450° C., with a 5 minute hold at 450° C. followed by gradual cooling to ambient temperature. Hydrophobicity testing was carried out as described in the Test Method above, the results are shown in Table 3. Organic Vapor Sensing Testing was carried out using the Test Method described above with the organic analytes acetone and toluene. The data are presented in FIGS. 2 (toluene) and 4 (acetone). X-ray Scattering analysis was carried out on a sample of Example 4 using the Test Method described above. The results of the test demonstrated no evidence for the presence of structural order. Both the low and wide angle data obtained were essentially featureless.

A sample of the coating solution used for Example 3 was used to prepare a sample to determine the pore size. Testing using the pore size determination test shown in the Test Methods above was carried out. The results of the test demonstrated that 75% of the total pore volume contained pores with a pore diameter of 2.0 nanometers or less, and 70% of the total pore volume contained pores with a diameter of 1.5 nanometers or less.

TABLE 1

| Example | Solution Used | Composition Ratio BTSBP:PTMS |
|---------|---------------|------------------------------|
| 1 | 1 | 100:0 |
| 2 | 2 | 90:10 |
| 3 | 3 | 80:20 |
| 4 | 4 | 70:30 |
| 5 | 5 | 60:40 |

Examples 6-10

Figure 3:
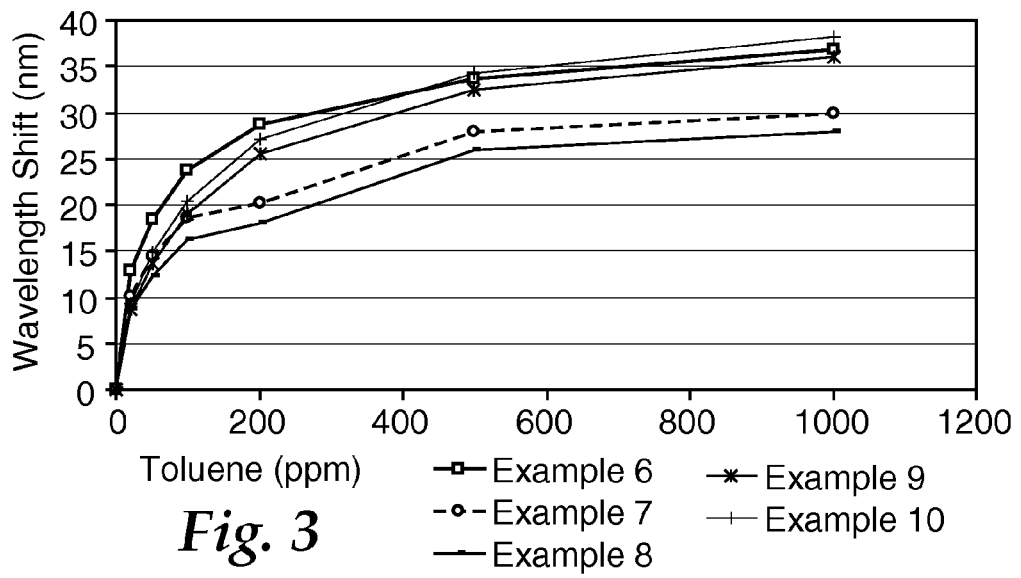
FIG. 3 is a plot of the measured wavelength shift of an exemplary sensing element at various exposure levels of the organic analyte toluene.
Figure 4:
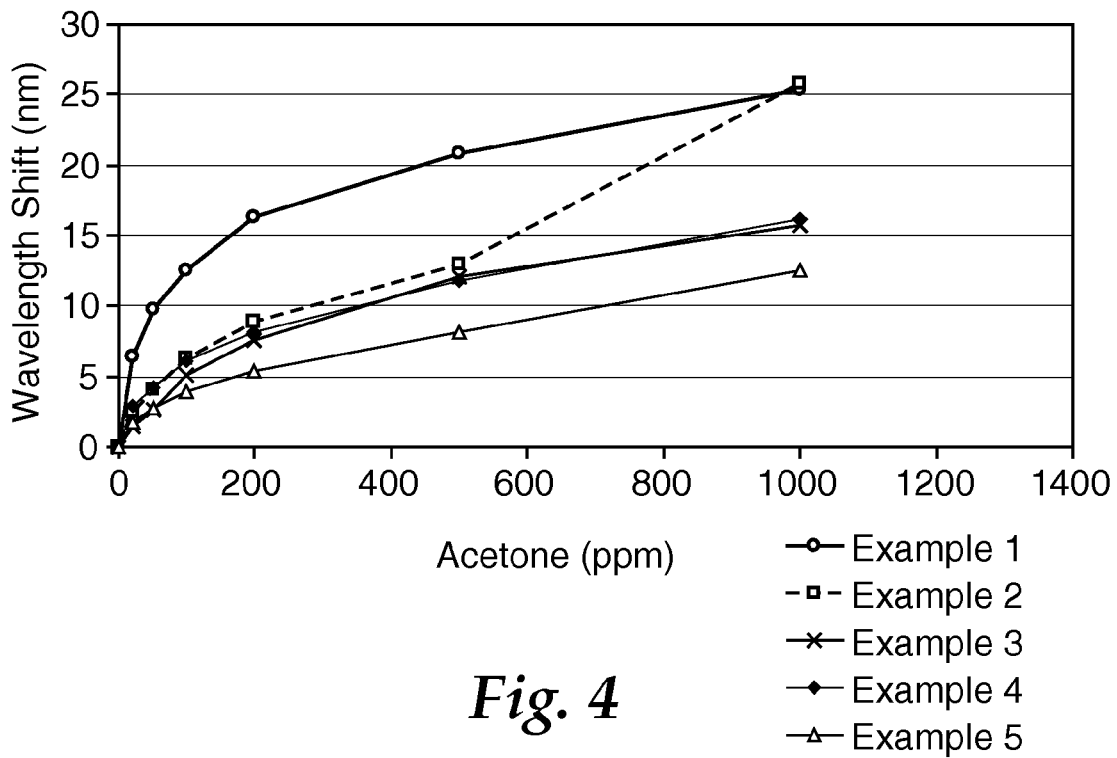
FIG. 4 is a plot of the measured wavelength shift of an exemplary sensing element at various exposure levels of the organic analyte acetone.
Figure 5:
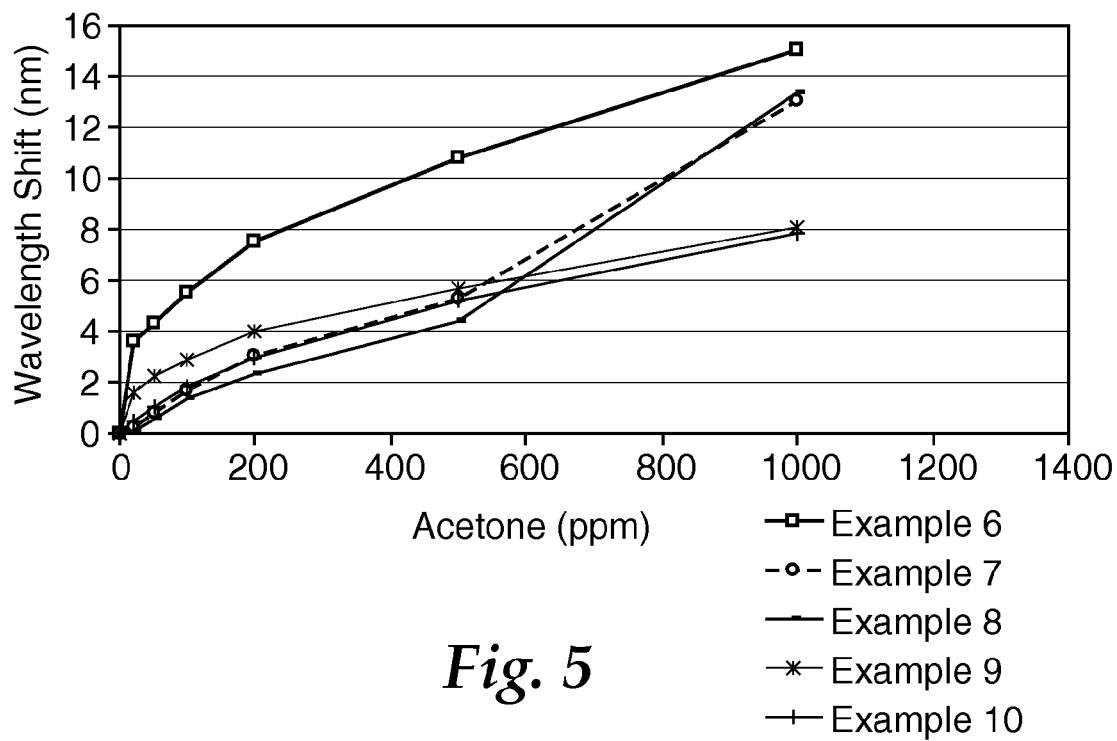
FIG. 5 is a plot of the measured wavelength shift of an exemplary sensing element at various exposure levels of the organic analyte acetone.

For Examples 6-10, the solutions shown in Table 2 were used. The solutions were spin coated onto Silicon Wafers using a Headway Research EC101 DT-R790 spin-coater with a 2 centimeter diameter chuck. Each Silicon Wafer section was flooded with several drops of solution prior to spinning The spin-coating was performed at 1000 rpm for 60 seconds. Coated sections were calcined in air in a box furnace at a rate of 1° C./min to a temperature of 450° C., with a 5 minute hold at 450° C. followed by gradual cooling to ambient temperature. Each of the Example coatings were post-treated by exposure to HMDS. The coated Silicon Wafers were placed into a polystyrene petri dish with a reservoir of HMDS (1-2 milliliters). The petri dish was covered, and the sections were allowed to react with HMDS vapor for 24 hours. Hydrophobicity testing was carried out as described in the Test Method above, the results are shown in Table 3. Organic Vapor Sensing Testing was carried out using the Test Method described above with the organic analytes acetone and toluene. The data are presented in FIGS. 3 (toluene) and 5 (acetone).

TABLE 2

| Example | Solution Used | Composition Ratio BTSBP:PTMS |
|---|---|---|
| 6 | 1 | 100:0 |
| 7 | 2 | 90:10 |
| 8 | 3 | 80:20 |
| 9 | 4 | 70:30 |
| 10 | 5 | 60:40 |

TABLE 3

| Example | $\Delta_{50\%}$ | $\Delta_{85\%}$ | Ratio $\Delta_{50\%}/\Delta_{85\%}$ | Pores filled (%) |
|---|---|---|---|---|
| 1 | 30.4 | 41.6 | 0.73 | 73% |
| 2 | 16.7 | 33.7 | 0.50 | 50% |
| 3 | 7.3 | 30.6 | 0.24 | 24% |
| 4 | 4.1 | 33.6 | 0.12 | 12% |
| 5 | 1.7 | 26.2 | 0.06 | 6% |
| 6 | 3.7 | 22.6 | 0.16 | 16% |
| 7 | 1.7 | 7.2 | 0.24 | 24% |
| 8 | 1.7 | 3.1 | 0.55 | 55% |
| 9 | 0.7 | 13.6 | 0.05 | 5% |
| 10 | 0.7 | 6.2 | 0.11 | 11% |

Example 11

A substrate was prepared by vapor depositing a 10 nanometer thick layer of titanium onto a 25×25 mm$^2$ section of glass plate. The titanium was coated by vapor deposition with a 20 nanometer thick layer of silicon oxide.

A coating solution was prepared by combining in a polyethylene bottle in order: OTAB (0.125 gram), ethanol (2.102 grams) BTSBP (0.398 gram), PTMS (0.103 gram) and 0.1 M HCl (aq) (0.201 gram).

A sample of this coating solution was used to prepare Example 11. After 121 minutes, the coating solution was spin-coated onto the substrate described above using a Headway Research EC101 DT-R790 spin-coater using a 2 centimeter diameter chuck. The section was flooded with several drops of solution prior to spinning The spin-coating was performed at 1000 rpm for 60 seconds. The coated sample was calcined in air in a furnace to a temperature of 450° C.

A 1.0 gram quantity of SILVERJETTMD GP 40LT-25C silver nanoparticles (43.25% in methanol, from Advanced Nano Products Co., Ltd., Korea) was added to 2 milliliters methanol to give a diluted suspension containing 16.8% solids. The diluted suspension was spin-coated at 600 rpm onto the organosilicate layer on the calcined sample. The sample was heated at 150° C. for 1 hour in air to partially sinter the silver particles.

What is claimed is:

1. A sensor comprising:
a substantially continuous first reflective layer;
a detection layer over the first reflective layer, the detection layer comprising a substantially microporous, amorphous, hydrophobic, analyte-responsive organosilicate material, wherein the substantially microporous, amorphous, hydrophobic, analyte-responsive organosilicate material comprises micropores which define a pore volume, and wherein the detection layer is prepared from a precursor mixture that is calcined.

2. The sensor of claim 1 further comprising:
a second reflective layer over the detection layer, the second reflective layer having an index of refraction different from the index of refraction of the detection layer, wherein at least a portion of the second reflective layer is permeable to an analyte.

3. The sensor of claim 1 wherein the substantially microporous, amorphous, hydrophobic, analyte-responsive organosilicate material adsorbs water into less than 50% of the available pore volume at a relative humidity of 50% at equilibrium.

4. The sensor of claim 1 wherein the substantially microporous, amorphous, hydrophobic, analyte-responsive organosilicate material does not display a detectable X-ray diffraction pattern when scanned from 0.5 to 80 degrees (2θ).

5. The sensor of claim 1 wherein at least 50% of the total pore volume comprises pores with a diameter of 2.0 nanometers or less.

6. The sensor of claim 1 wherein at least 50% of the total pore volume comprises pores with a diameter of 0.6-1.3 nanometers.

7. The sensor of claim 2, wherein one or both of the first or second reflective layers comprises a metal.

8. The sensor of claim 2, wherein the second reflective layer is a semi-reflective layer that is a substantially continuous layer.

9. The sensor of claim 2, wherein the second reflective layer has a differential permeability such that the second reflective layer has a higher analyte permeability at a first location on an upper surface of the second reflective layer and a lower analyte permeability at a second location on the upper surface.

10. The sensor of claim 9, wherein the first and second locations form a pattern on the upper surface of the second reflective layer.

11. The sensor of claim 2, wherein the second reflective layer comprises a single layer of semi-reflective material on an outer surface of the detection layer opposite the first reflective layer.

12. The sensor of claim 11, wherein the first reflective layer comprises a single layer of reflective material.

13. The sensor of claim 2, wherein the sensor further comprises a masking layer over at least a portion of the second reflective layer.

14. The sensor of claim 1, wherein the first reflective layer comprises silver.

15. The sensor of claim 1, wherein the detection layer has a first thickness in a first location of the detection layer and a second thickness in a second location of the detection layer, said second thickness being different from said first thickness.

16. The sensor of claim 1, wherein at least a portion of the first reflective layer is permeable to said analyte.

17. The sensor of claim 2, wherein the sensor is substantially free of analyte, and either displays a first color or is colorless when viewed through the second reflective layer.

18. An array comprising two or more sensors, wherein the sensors comprise:
a substantially continuous first reflective layer;
a detection layer over the first reflective layer, the detection layer comprising a substantially microporous, amorphous, hydrophobic, analyte-responsive organosilicate material, wherein the substantially microporous, amorphous, hydrophobic, analyte-responsive organosilicate material comprises micropores which define a pore volume, and wherein the detection layer is prepared from a precursor mixture that is calcined.

19. The array of claim 18 wherein the sensors further comprise:
a second reflective layer over the detection layer, the second reflective layer having an index of refraction different from the index of refraction of the detection layer, wherein at least a portion of the second reflective layer is permeable to an analyte.

20. The array of claim 18, wherein at least two sensors in the array have different detection layer pore size distributions, different detection layer thicknesses, or a combination thereof.

21. The sensor of claim 2 further comprising a housing at least partially enclosing the sensor, wherein the housing comprises at least one opening positioned above the second reflective layer, said at least one opening providing a restricted view of an upper surface of the second reflective layer, wherein the restricted view allows a view of the upper surface of the second reflective layer within an angle of ±30° from a normal view.

22. A device comprising:
a substantially continuous first reflective layer;
a detection layer over the first reflective layer, the detection layer comprising a substantially microporous, amorphous, hydrophobic, analyte-responsive organosilicate material, wherein the substantially microporous, amorphous, hydrophobic, analyte-responsive organosilicate material comprises micropores which define a pore volume, and wherein the detection layer is prepared from a precursor mixture that is calcined; and
a light source.

23. The device of claim 22 further comprising:
a second reflective layer over the detection layer, the second reflective layer having an index of refraction different from the index of refraction of the detection layer, wherein at least a portion of the second reflective layer is permeable to an analyte.

24. The device of claim 22, further comprising a photodetector.

25. A method of detecting the presence or absence of an analyte, the method comprising:
providing a sensor comprising:
a substantially continuous first reflective layer;
a detection layer over the first reflective layer, the detection layer comprising a substantially microporous, amorphous, hydrophobic, analyte-responsive organosilicate material, wherein the substantially microporous, amorphous, hydrophobic, analyte-responsive organosilicate material comprises micropores which define a pore volume, and wherein the detection layer is prepared from a precursor mixture that is calcined;
providing a light source;
contacting the sensor with a medium that may contain an analyte; and
monitoring the sensor for a change in optical properties.

26. The method of claim 25 wherein the sensor further comprises:
a second reflective layer over the detection layer, the second reflective layer having an index of refraction different from the index of refraction of the detection layer, wherein at least a portion of the second reflective layer is permeable to an analyte.

27. The method of claim 25, wherein the change in optical properties produces a visible change.

28. The method of claim 25, wherein the medium is a gas or a liquid.

29. The method of claim 26, wherein the analyte permeates through the second reflective layer, the first reflective layer, or both.

* * * * *